(12) United States Patent
Takahashi et al.

(10) Patent No.: US 10,520,416 B2
(45) Date of Patent: Dec. 31, 2019

(54) SUBSTRATE TREATING METHOD FOR A SUBSTRATE TREATING APPARATUS THAT CARRIES OUT ETCHING TREATMENT OF SUBSTRATES

(71) Applicant: SCREEN Holdings Co., Ltd., Kyoto (JP)

(72) Inventors: Tomohiro Takahashi, Kyoto (JP); Hiroyuki Araki, Kyoto (JP)

(73) Assignee: SCREEN Holdings Co., Ltd. (JP)

( * ) Notice: Subject to any disclaimer, the term of this patent is extended or adjusted under 35 U.S.C. 154(b) by 0 days.

(21) Appl. No.: 15/438,341

(22) Filed: Feb. 21, 2017

(65) Prior Publication Data
US 2017/0160181 A1  Jun. 8, 2017

Related U.S. Application Data

(62) Division of application No. 13/744,879, filed on Jan. 18, 2013, now abandoned.

(30) Foreign Application Priority Data

Mar. 27, 2012  (JP) ................................ 2012-071556

(51) Int. Cl.
*G01N 15/06* (2006.01)
*H01L 21/306* (2006.01)
(Continued)

(52) U.S. Cl.
CPC ......... *G01N 15/0656* (2013.01); *C01B 25/18* (2013.01); *C09K 13/04* (2013.01);
(Continued)

(58) Field of Classification Search
CPC ......... H01L 21/67086; H01L 21/67057; H01L 21/30604; H01L 21/31111; G01N 15/0656
See application file for complete search history.

(56) References Cited

U.S. PATENT DOCUMENTS 3,924,175 A    12/1975  Wilson .......................... 204/400
5,000,207 A *  3/1991  Titterington ...... H01L 21/67051
                                                        134/147
(Continued)

FOREIGN PATENT DOCUMENTS

CN  1289860 A   4/2001
CN  1712567 A   12/2005
(Continued)

OTHER PUBLICATIONS

Korean Office Action dated Jan. 27, 2014, issued in corresponding Korean Patent Application No. 10-2013-0028610 (4 pages).
(Continued)

*Primary Examiner* — Allan W. Olsen
*Assistant Examiner* — Margaret D Klunk
(74) *Attorney, Agent, or Firm* — Ostrolenk Faber LLP

(57) ABSTRACT

A substrate treating apparatus includes a circulating line having a treating tank for storing a phosphoric acid aqueous solution, a circulating pump for feeding the phosphoric acid aqueous solution, a heater for circulation for heating the phosphoric acid aqueous solution, a filter for filtering the phosphoric acid aqueous solution, the circulating line causing the phosphoric acid aqueous solution discharged from the treating tank to flow in order of the circulating pump, the heater for circulation and the filter, and returning the phosphoric acid aqueous solution from the filter to the treating tank. The apparatus also includes a branch pipe branching from the circulating line between the heater for circulation and the filter for extracting the phosphoric acid aqueous solution from the circulating line, and a concentration measuring station connected to the branch pipe for measuring silicon concentration in the phosphoric acid aqueous solution by potentiometry.

12 Claims, 4 Drawing Sheets

(51) Int. Cl.
*H01L 21/67* (2006.01)
*H01L 21/311* (2006.01)
*C01B 25/18* (2006.01)
*C09K 13/04* (2006.01)
*C11D 7/08* (2006.01)
*C11D 11/00* (2006.01)
*G01N 27/416* (2006.01)

(52) U.S. Cl.
CPC ............ *C11D 7/08* (2013.01); *C11D 11/0047* (2013.01); *G01N 27/4161* (2013.01); *H01L 21/30604* (2013.01); *H01L 21/31111* (2013.01); *H01L 21/67057* (2013.01); *H01L 21/67086* (2013.01)

(56) References Cited

U.S. PATENT DOCUMENTS

| | | | |
|---|---|---|---|
| 5,376,214 A | 12/1994 | Iwasaki et al. | 156/345 |
| 6,399,517 B2 | 6/2002 | Yokomizo et al. | 438/745 |
| 6,623,183 B2 | 9/2003 | Nakagawa et al. | 396/578 |
| 6,780,277 B2 | 8/2004 | Yokomizo et al. | 156/345.11 |
| 7,635,397 B2 | 12/2009 | Okuchi | 29/25.01 |
| 8,008,087 B1 * | 8/2011 | Shalyt | G01N 27/4166 436/124 |
| 8,211,810 B2 | 7/2012 | Kiyose | 438/753 |
| 8,409,997 B2 * | 4/2013 | Wei | H01L 21/31111 216/83 |
| 2002/0061605 A1 | 5/2002 | Hasegawa et al. | 438/5 |
| 2006/0263251 A1 | 11/2006 | Watatsu et al. | 422/68.1 |
| 2006/0263257 A1 * | 11/2006 | Beauchamp | G01N 21/783 422/88 |
| 2008/0066863 A1 | 3/2008 | Kiyose et al. | 156/345.15 |
| 2008/0179293 A1 | 7/2008 | Wei et al. | 216/84 |
| 2013/0240143 A1 | 9/2013 | Kiyose et al. | 156/345.15 |

FOREIGN PATENT DOCUMENTS

| | | |
|---|---|---|
| CN | 101150066 A | 3/2008 |
| JP | 05-198555 | 8/1993 |
| JP | 06-104243 | 4/1994 |
| JP | 08-083792 A | 3/1996 |
| JP | 09-129588 A | 5/1997 |
| JP | 11-142332 | 5/1999 |
| JP | 11-145107 A | 5/1999 |
| JP | 2001-250804 | 9/2001 |
| JP | 2003-297798 | 10/2003 |
| JP | 2006-352097 A | 12/2006 |
| JP | 2008-103678 | 5/2008 |
| JP | 2012-28580 A | 2/2012 |
| KR | 10-2008-0026489 | 3/2008 |

OTHER PUBLICATIONS

Chinese Office Action and search report dated Nov. 26, 2014, issued in corresponding Chinese Patent Application No. 201310055320.2.
Second Chinese Office Action dated Jul. 21, 2015 for corresponding Chinese Patent Application No. 201310055320.2.
Notification of Reasons for Refusal dated Jun. 2, 2015 in corresponding JP Application No. 2012-071556.
Notice of Allowance dated Jul. 28, 2015 in corresponding JP Application No. 2012-071556.

* cited by examiner

SUBSTRATE TREATING METHOD FOR A SUBSTRATE TREATING APPARATUS THAT CARRIES OUT ETCHING TREATMENT OF SUBSTRATES

CROSS REFERENCE TO RELATED APPLICATION

This application is a divisional of U.S. patent application Ser. No. 13/744,879, filed Jan. 18, 2013, which claims the benefit of Japanese Patent Application No. 2012-071556, filed Mar. 27, 2012, which is incorporated herein by reference.

BACKGROUND OF THE INVENTION (1) Field of the Invention

This invention relates to a substrate treating apparatus for treating semiconductor wafers, substrates for liquid crystal displays, substrates for plasma displays, substrates for organic EL, substrates for FEDs (Field Emission Displays), substrates for optical displays, substrates for magnetic disks, substrates for magnetic optical disks, substrates for photomasks, substrates for solar cells and so on (hereinafter simply called substrates). More particularly, the invention relates a technique of treating substrates by immersing the substrates in a phosphoric acid aqueous solution.

(2) Description of the Related Art

Conventionally, this type of apparatus includes a treating tank, a pump, a heater and a filter which constitute a circulating line. The treating tank stores a phosphoric acid aqueous solution, and substrates are immersed in the phosphoric acid aqueous solution for treatment. The phosphoric acid aqueous solution discharged from the treating tank is returned to the treating tank again via the pump, heater and filter. A silicon concentration meter is mounted on this circulating line. The silicon concentration meter measures silicon concentration by detecting absorbance of a specific wavelength based on light transmitted through the phosphoric acid aqueous solution (as disclosed in Japanese Unexamined Patent Publication No. 2008-103678, for example).

The substrate treating apparatus constructed in this way can measure silicon concentration in the phosphoric acid aqueous solution flowing through the circulating line. Based on the measurement result, the silicon concentration in the phosphoric acid aqueous solution can be adjusted. Adjustment of the silicon concentration will be described. An example is here taken of a treatment of substrates having silicon oxide film and silicon nitride film formed thereon, in which the silicon nitride film is selectively etched, leaving the silicon oxide film on the substrates. In this case, the higher silicon concentration will result in the lower etching rate of the silicon nitride film, and the greater increase in the quantity of particles in the phosphoric acid aqueous solution, thereby shortening the life of the phosphoric acid aqueous solution. On the other hand, the lower silicon concentration will result in even the silicon oxide film etched more than is needed (i.e. will lower etching selectivity for the silicon nitride film). Therefore, the silicon concentration is adjusted within a predetermined range for inhibiting lowering of the etching selectivity while inhibiting lowering of the etching rate of the silicon nitride film.

However, the conventional example with such construction has the following problems.

The conventional apparatus, since the silicon concentration is estimated from the absorbance of the phosphoric acid aqueous solution, has an inconvenience that the accuracy of the measurement result of the silicon concentration is not so high. Since absorbance is easily influenced by the temperature of the phosphoric acid aqueous solution, there is an inconvenience that large temperature changes of the phosphoric acid aqueous solution render the accuracy of the measurement result unstable (variable).

SUMMARY OF THE INVENTION

This invention has been made having regard to the state of the art noted above, and its object is to provide a substrate treating apparatus capable of measuring silicon concentration in a phosphoric acid aqueous solution with high accuracy.

To solve the above problems of the prior art, Inventors have made intensive research and attained the following findings.

It has been found that potentiometry can improve the accuracy of measuring silicon concentration in the phosphoric acid aqueous solution.

This potentiometry adds a reagent to the phosphoric acid aqueous solution, places a measuring electrode and a reference electrode in contact with the solution, respectively, and measures a potential difference between the measuring electrode and the reference electrode, thereby to measure the silicon concentration in the phosphoric acid aqueous solution. Here, the solution to which the reagent has been added cannot be returned again to the circulating line. It has been found therefore that, when a concentration measuring device using potentiometry is employed, the concentration measuring device cannot be provided on the circulating line as in the conventional technique. It has also been found that, when the concentration measuring device using potentiometry is employed, the temperature of the phosphoric acid aqueous solution extracted from the circulating line lowers, and there is a possibility that silicon and other substances deposit in the phosphoric acid aqueous solution.

Based on the above findings, this invention provides the following construction.

A substrate treating apparatus according to this invention comprises a circulating line including a treating tank for storing a phosphoric acid aqueous solution, a circulating pump for feeding the phosphoric acid aqueous solution, a heater for circulation for heating the phosphoric acid aqueous solution, a filter for filtering the phosphoric acid aqueous solution, the circulating line causing the phosphoric acid aqueous solution discharged from the treating tank to flow in order of the circulating pump, the heater for circulation and the filter, and returning the phosphoric acid aqueous solution from the filter to the treating tank; a branch pipe branching from the circulating line between the heater for circulation and the filter for extracting the phosphoric acid aqueous solution from the circulating line; and a concentration measuring station connected to the branch pipe for measuring silicon concentration in the phosphoric acid aqueous solution by potentiometry.

The substrate treating apparatus according to this invention, with the concentration measuring station using potentiometry, can measure silicon concentration in the phosphoric acid aqueous solution with high accuracy. The apparatus has the branch pipe also, and the phosphoric acid aqueous solution fed from the circulating line to the concentration measuring station does not return to the circulating line. Thus, there is no possibility that a reagent or the like used in the concentration measuring station mixes into the circulating line. Since the branch pipe branches from the circulating line between the heater for circulation and the filter, part of the phosphoric acid aqueous solutions flowing through the circulating line can be extracted in a condition of relatively high temperature. This can inhibit silicon and other substances from depositing in the extracted phosphoric acid aqueous solution. As a result, the accuracy of silicon concentration measurement can be further improved.

The phrase "between the heater for circulation and the filter" embraces the heater for circulation itself and the filter itself, besides the pipeline connecting the heater for circulation and the filter. Therefore, for example, a construction in which the branch pipe is joined to the filter is also included in the meaning of "between the heater for circulation and the filter".

The substrate treating apparatus according to this invention may further comprise a heater for sampling for heating the phosphoric acid aqueous solution extracted from the circulating line. With the heater for sampling, silicon and other substances can be properly inhibited from depositing in the phosphoric acid aqueous solution extracted from the circulating line.

In another aspect of the invention, a substrate treating apparatus comprises a circulating line including a treating tank for storing a phosphoric acid aqueous solution, a circulating pump for feeding the phosphoric acid aqueous solution, a heater for circulation for heating the phosphoric acid aqueous solution, a filter for filtering the phosphoric acid aqueous solution, the circulating line causing the phosphoric acid aqueous solution discharged from the treating tank to flow in order of the circulating pump, the heater for circulation and the filter, and returning the phosphoric acid aqueous solution from the filter to the treating tank; a branch pipe branching from the circulating line for extracting the phosphoric acid aqueous solution from the circulating line; a concentration measuring station connected to the branch pipe for measuring, by potentiometry, silicon concentration in the phosphoric acid aqueous solution extracted; and a heater for sampling for heating the phosphoric acid aqueous solution drawn from the circulating line.

The above substrate treating apparatus according to this invention, with the concentration measuring station using potentiometry, can measure silicon concentration in the phosphoric acid aqueous solution with high accuracy. The apparatus has the branch pipe also, and the phosphoric acid aqueous solution fed from the circulating line to the concentration measuring station does not return to the circulating line. Thus, there is no possibility that a reagent or the like used in the concentration measuring station mixes into the circulating line. With the heater for sampling, silicon and other substances can be properly inhibited from depositing in the phosphoric acid aqueous solution extracted from the circulating line. As a result, the accuracy of silicon concentration measurement can be further improved.

In the invention noted above, the heater for sampling may be mounted on the branch pipe for heating the phosphoric acid aqueous solution in the branch pipe. This construction can conveniently heat the phosphoric acid aqueous solution flowing through the branch pipe.

In the invention noted above, the heater for sampling may be attached to the concentration measuring station for heating the phosphoric acid aqueous solution or a solution including the phosphoric acid aqueous solution in the concentration measuring station. With this construction, even if silicon and other substances started depositing in the phosphoric acid aqueous solution, the silicon and other substances could be redissolved in the phosphoric acid aqueous solution or the solution including the phosphoric acid aqueous solution within the concentration measuring station. This can properly prevent lowering of the measurement accuracy of the concentration measuring station.

The above substrate treating apparatus may further comprise a quantity measuring station connected to the branch pipe for measuring a predetermined quantity of the phosphoric acid aqueous solution; wherein the concentration measuring station is arranged to measure silicon concentration in the phosphoric acid aqueous solution measured by the quantity measuring station, and the heater for sampling is attached to the quantity measuring station for heating the phosphoric acid aqueous solution in the quantity measuring station. This can inhibit silicon and other substances from depositing in the phosphoric acid aqueous solution measured in the quantity measuring station. Thus, the quantity measuring station can measure the phosphoric acid aqueous solution with increased accuracy. Since the quantity measuring station is provided separately from the concentration measuring station, there is no need to measure the phosphoric acid aqueous solution in the concentration measuring station. This can shorten the time taken by the concentration measuring station in measuring silicon concentration.

The above substrate treating apparatus may further comprise a quantity measuring station connected to the branch pipe for measuring a predetermined quantity of the phosphoric acid aqueous solution; wherein the concentration measuring station is arranged to measure silicon concentration in the phosphoric acid aqueous solution measured by the quantity measuring station. Since the quantity measuring station is provided separately from the concentration measuring station, there is no need to measure the phosphoric acid aqueous solution in the concentration measuring station. This can shorten the time taken by the concentration measuring station in measuring silicon concentration.

In the invention noted above, the quantity measuring station may include a measuring tank for storing the predetermined quantity of the phosphoric acid aqueous solution. With this construction, the quantity measuring station can conveniently measure the phosphoric acid aqueous solution. In this invention, it is preferred that the heater for sampling is attached to the measuring tank for heating the phosphoric acid aqueous solution in the measuring tank. This can properly prevent lowering of measuring accuracy.

In the invention noted above, the quantity measuring station may include a syringe having a cylindrical shape; a plunger slidable inside the syringe in an airtight condition; and a driver for driving the plunger to draw into and discharge from the syringe the predetermined quantity of the phosphoric acid aqueous solution. With this construction, the quantity measuring station can conveniently measure the phosphoric acid aqueous solution. In this invention, it is preferred that the heater for sampling is attached to the measuring tank for heating the phosphoric acid aqueous solution in the measuring tank. This can properly prevent lowering of measuring accuracy.

In the invention noted above, the treating tank may include an inner tank for immersing substrates in the phosphoric acid aqueous solution stored therein; and an outer tank for collecting the phosphoric acid aqueous solution overflowing from the inner tank; the filter may include a filter element formed between an entrance portion and an exit portion thereof, and the circulating line may include a first piping connecting the exit portion of the filter and the inner tank; and a second piping connecting the entrance portion of the filter and the outer tank; the branch pipe branching from the second piping. The second piping has a higher inner pressure than the first piping. Since the branch pipe branches from the second piping, part of the phosphoric acid aqueous solution can be drawn easily from the circulating line. Further, the phosphoric acid aqueous solution in the second piping, which has not passed through the filter element, has a higher temperature than the phosphoric acid aqueous solution in the first piping. Thus, the phosphoric acid aqueous solution can be extracted in a condition of higher temperature.

This specification discloses the following features of the invention also:

(1) In the invention noted above, a temperature to which the heater for sampling heats the extracted phosphoric acid aqueous solution may be substantially the same as a temperature to which the heater for circulation heats the phosphoric acid aqueous solution.

With the construction noted in paragraph (1) above, the conditions of the phosphoric acid aqueous solution can be made substantially the same in the circulating line and the concentration measuring station. Therefore, the silicon concentration in the phosphoric acid aqueous solution flowing through the circulating line can be grasped conveniently.

(2) In the invention noted above, the branch pipe may have a switch vale mounted in an intermediate position thereof.

With the construction noted in paragraph (2) above, since the circulating line has no switch valve mounted thereon, the phosphoric acid aqueous solution can be made to flow continuously through the circulating line even when the phosphoric acid aqueous solution is extracted from the circulating line. It is also possible to inhibit an increase in pressure loss occurring in the circulating line.

(3) In the invention noted above, the apparatus may further comprise a selector valve disposed at a joint of the circulating line and the branch pipe for switching a flow path of the phosphoric acid aqueous solution.

With the construction noted in paragraph (3) above, the flow path of the phosphoric acid aqueous solution can be conveniently switched between the circulating line and the branch pipe.

(4) In the invention noted above, the concentration measuring station may include a measuring vessel for receiving the phosphoric acid aqueous solution and the reagent supplied, a measuring electrode disposed to contact the solution in the measuring vessel, a reference electrode disposed to contact the solution in the measuring vessel, and a potentiometric unit for measuring a potential difference between the measuring electrode and the reference electrode.

The construction noted in paragraph (4) above can measure silicon concentration conveniently.

(5) In the invention noted above, the heater for sampling may be attached to the measuring vessel for heating the solution in the measuring vessel.

With the construction noted in paragraph (5) above, even if silicon and other substances started depositing in the phosphoric acid aqueous solution, the silicon and other substances could be redissolved within the concentration measuring station. This can properly prevent lowering of the measurement accuracy of the concentration measuring station.

(6) In the invention noted above, the concentration measuring station may further include a drain pipe connected to the measuring vessel for disposing of the solution in the measuring vessel.

The construction noted in paragraph (6) above can conveniently dispose of the phosphoric acid aqueous solution used in the concentration measuring station.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

DESCRIPTION OF THE PREFERRED EMBODIMENTS

Preferred embodiments of this invention will be described in detail hereinafter with reference to the drawings.

Embodiment 1

Embodiment 1 of this invention will be described hereinafter with reference to a drawing.

Embodiment 1 will be described taking, as an example, an apparatus for immersing substrates (e.g. semiconductor wafers) having silicon oxide film and silicon nitride film formed thereon in a phosphoric acid aqueous solution produced by mixing phosphoric acid and deionized water, to carry out etching treatment for selectively etching the silicon nitride film.

Figure 1:
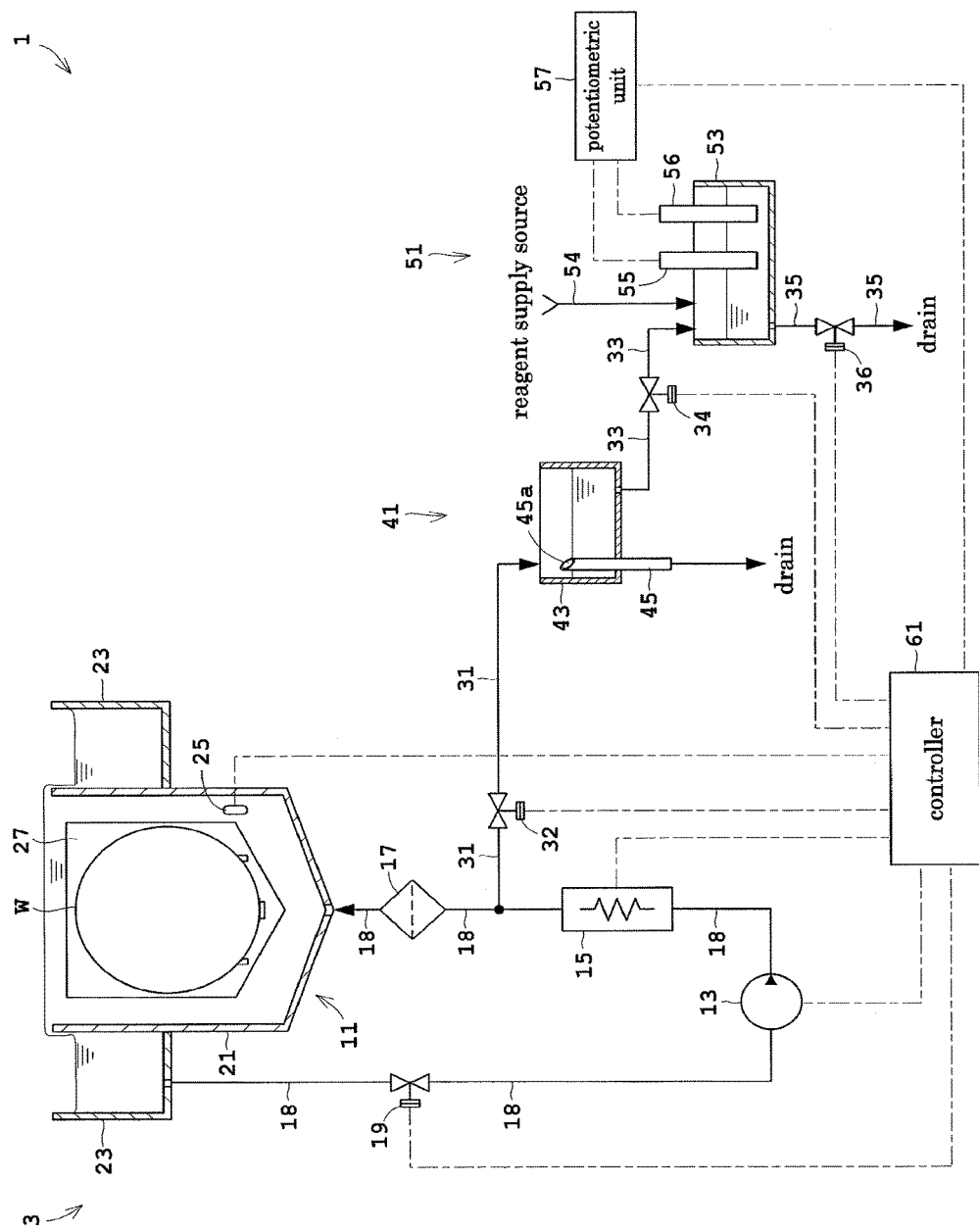
FIG. 1 is a view showing an outline construction of a substrate treating apparatus according to Embodiment 1.

FIG. 1 shows an outline construction of a substrate treating apparatus 1 according to Embodiment 1. The substrate treating apparatus 1 has a circulating line 3 for circulating the phosphoric acid aqueous solution. The circulating line 3 includes a treating tank 11, a circulating pump 13, a heater 15 for circulation and a filter 17. The treating tank 11 stores the phosphoric acid aqueous solution. The circulating pump 13 feeds the phosphoric acid aqueous solution under pressure. The heater 15 for circulation heats the phosphoric acid aqueous solution. The filter 17 filters the phosphoric acid aqueous solution. The circulating line 3 further includes a pipeline 18 which interconnects the treating tank 11, circulating pump 13, heater 15 for circulation and filter 17. A switch valve 19 is mounted on the pipeline 18 between the treating tank 11 and circulating pump 13. The switch valve 19 is also an element of the circulating line 3.

The phosphoric acid aqueous solution flows through the circulating line 3 constructed in this way. Specifically, the phosphoric acid aqueous solution flows through the treating tank 11, circulating pump 13, heater 15 for circulation and filter 17 in the stated order, and returns from the filter 17 to the treating tank 11.

The treating tank 11 has an inner tank 21 and an outer tank 23. The inner tank 21 stores the phosphoric acid aqueous solution. The inner tank 21 has a temperature sensor 25 disposed therein for detecting the temperature of the phosphoric acid aqueous solution. The bottom of the inner tank 21 is connected to the second side of the filter 17 through the pipeline 18. The outer tank 23 is formed outside an upper edge of the inner tank 21 for collecting the phosphoric acid aqueous solution overflowing the inner tank 21. The outer tank 23 is connected to the primary side of the circulating pump 13 through the pipeline 18. The "secondary side" is synonymous with a downstream side with respect of the flowing direction of the phosphoric acid aqueous solution. The "primary side" is the opposite of the "secondary side".

The substrate treating apparatus 1 has a lifter 27 for immersing wafers W in the phosphoric acid aqueous solution. The lifter 27 holds a plurality of wafers W in an upstanding posture, and moves the wafers W between a "treating position" (position shown in solid lines in FIG. 1) inside the inner tank 21 and a "transfer position" above the inner tank 21. When in the treating position, the wafers W are immersed in the phosphoric acid aqueous solution within the inner tank 21. In the transfer position, the lifter 27 can transfer the wafers W to and from a separate transport mechanism.

The substrate treating apparatus 1 further includes a branch pipe 31 branching from the circulating line 3, a quantity measuring station 41 connected to this branch pipe 31, and a concentration measuring station 51. The phosphoric acid aqueous solution flows from one end joined to the circulating line 3 toward the other end of the branch pipe 31.

The one end of the branch pipe 31 is connected to the pipeline 18 between the heater 15 for circulation and the filter 17. The other end of the branch pipe 31 is connected to the quantity measuring station 41. The branch pipe 31 has a switch valve 32 mounted in an intermediate position thereof.

The quantity measuring station 41 measures a predetermined quantity (volume) of the phosphoric acid aqueous solution. The quantity measuring station 41 has a measuring tank 43 and an overflow pipe 45. The phosphoric acid aqueous solution is supplied to the measuring tank 43 from the secondary side of the branch pipe 31. The overflow pipe 45 adjusts the phosphoric acid aqueous solution in the measuring tank 43 to the predetermined quantity. Specifically, the overflow pipe 45 is disposed to penetrate the measuring tank 43, with one end region of the overflow pipe 45 inserted into the interior of the measuring tank 43. An opening 45*a* is formed in a predetermined height position at one end of the overflow pipe 45. When the liquid level of the phosphoric acid aqueous solution in the measuring tank 43 exceeds the height position of the opening 45*a*, the phosphoric acid aqueous solution will flow into the overflow pipe 45 through the opening 45*a*, to be discharged (disposed of) to the exterior of the measuring tank 43. As a result, the measuring tank 43 does not store the phosphoric acid aqueous solution in excess of the predetermined quantity corresponding to the height position of the opening 45*a*.

A feed pipe 33 extends between the quantity measuring station 41 and the concentration measuring station 51. One end of the feed pipe 33 is connected to the measuring tank 43. The feed pipe 33 has a switch valve 34 mounted in an intermediate position thereof.

The concentration measuring station 51 measures silicon concentration in the phosphoric acid aqueous solution by potentiometry. The silicon concentration is a concentration of silicon compounds including siloxane and so on.

The concentration measuring station 51 has a measuring vessel 53, a reagent feeder 54, a measuring electrode 55, a reference electrode 56 and a potentiometric unit 57. The measuring vessel 53 receives the phosphoric acid aqueous solution from the other end of the feed pipe 33, and a reagent in a predetermined quantity from the reagent feeder 54. The quantity (volume) and concentration of the reagent supplied from the reagent feeder 54 are known. The measuring electrode 55 and reference electrode 56 are arranged to contact the solution in the measuring vessel 53, respectively.

The potentiometric unit 57 measures a potential difference between the measuring electrode 55 and reference electrode 56, and measures silicon concentration based on this measurement result.

What to use as the above reagent may be selected as appropriate. For example, fluoride ions may be used as the reagent, and a fluoride-ion selective electrode as the measuring electrode 55. In this case, a concentration of fluoride ions can be measured directly. Here, fluoride ions react with silicon compounds and the concentration of fluoride ions lowers accordingly. That is, the concentration of fluoride ions corresponds conveniently to silicon concentration. Therefore, based on the concentration of fluoride ions, the silicon concentration present in the phosphoric acid aqueous solution can be measured (estimated) with high accuracy.

A drain pipe 35 is connected to the measuring vessel 53 for draining the solution used in measuring silicon concentration. The drain pipe 35 has a switch valve 36 mounted thereon. When the switch valve 36 is opened, the solution in the measuring vessel 53 is disposed of through the drain pipe 35.

The substrate treating apparatus 1 further includes a controller 61 for performing overall control of the various components described above. Specifically, the controller 61 receives detection results from the temperature sensor 25 and measurement results from the concentration measuring station 51. Based on these detection results and measurement results and a recipe specifying a treating procedure and treating conditions, the controller 61 controls the circulating pump 13, heater 15 for circulation, lifter 27, switch valves 19, 32, 34 and 36, and potentiometric unit 57. The controller 61 has a central processing unit (CPU) which performs various processes, a RAM (Random-Access Memory) for providing workspace for arithmetic processes, and a storage medium such as a fixed disk for storing various information such as the recipe.

Next, an example of operation of the substrate treating apparatus 1 according to Embodiment 1 will be described. Here, the substrate treating apparatus 1 first carries out substrate treatment, and thereafter measures concentration.

1. Substrate Treatment

The controller 61 drives the circulating pump 13 in a state where the switch valve 19 is opened and the switch valves 32, 34 and 36 are closed. The phosphoric acid aqueous solution is fed under pressure by the circulating pump 13 to flow through the circulating line 3. That is, the phosphoric acid aqueous solution, after being discharged from the treating tank 11 (outer tank 23), flows through the circulating pump 13, heater 15 for circulation and filter 17 in the stated order, and returns from the filter 17 to the treating tank 11 (inner tank 21) again. Foreign substances and particles present in the phosphoric acid aqueous solution are removed by the filter 17. Within the inner tank 21, upflows of the phosphoric acid aqueous solution are formed to move upward from the bottom of the inner tank 21. The phosphoric acid aqueous solution overflowing the inner tank 21 proceeds to the outer tank 23.

Based on a detection result of the temperature sensor 25, the controller 61 controls the heater 15 for circulation so that the temperature of the phosphoric acid aqueous solution in the inner tank 21 become a predetermined target temperature (target value). The target value is 160 degrees, for example. However, the target value is not limited to this, but may be selected to be or changed to a different temperature or temperature range as appropriate. When the temperature of the phosphoric acid aqueous solution in the inner tank 21 is stable at the target value, the quantity of heat which the heater 15 for circulation gives to the phosphoric acid aqueous solution is sufficient if it is substantially equivalent to the heat released from the phosphoric acid aqueous solution during one circuit through the circulating line 3. The phosphoric acid aqueous solution in the circulating line 3 has a temperature distribution which is the highest at the exit (secondary side) of the heater 15 for circulation, and the lowest at the entrance (primary side) of the heater 15 for circulation.

The lifter 27 is lowered in the state of the phosphoric acid aqueous solution flowing through the circulating line 3 as described above. The plurality of wafers W held by the lifter 27 descend from the transfer position to the treating position to be immersed in the phosphoric acid aqueous solution inside the inner tank 21. This starts etching treatment of the silicon nitride film formed on each wafer W. Upon lapse of a predetermined time, the lifter 27 is raised. The wafers W ascend from the treating position to the transfer position to be withdrawn from the phosphoric acid aqueous solution. This completes the etching treatment of the plurality of wafers W.

2. Concentration Measurement

Next, the controller 61 opens the switch valve 32 while continuing to drive the circulating pump 13. Part of the phosphoric acid aqueous solution flowing through the circulating line 3 flows into the branch pipe 31. The phosphoric acid aqueous solution having flowed into the branch pipe 31 is supplied to the measuring tank 43. When the phosphoric acid aqueous solution stored in the measuring tank 43 exceeds the predetermined quantity, an excess part is discharged from the measuring tank 43 by way of the overflow pipe 45. As a result, the phosphoric acid aqueous solution remains in the measured predetermined quantity in the measuring tank 43.

Then, the switch valve 34 is opened. The predetermined quantity of phosphoric acid aqueous solution is supplied from the measuring tank 43 to the measuring vessel 53 through the feed pipe 33. The reagent feeder 54 supplies a predetermined quantity of reagent to the measuring vessel 53. The phosphoric acid aqueous solution and the reagent are mixed within the measuring vessel 53. The potentiometric unit 57 measures a potential difference between the measuring electrode 55 and reference electrode 56, and measures a silicon concentration based on this measurement result. When the measurement is completed, the switch valve 36 is opened. The solution in the measuring vessel 53 is drained through the drain pipe 35.

The controller 61, based on the measurement result by the concentration measuring station 51, grasps conditions of the phosphoric acid aqueous solution flowing through the circulating line 3, and determines contents of subsequent treatment. When, for example, the silicon concentration is within a predetermined range, new etching treatment is started using the phosphoric acid aqueous solution flowing through the circulating line 3. On the other hand, when the silicon concentration is not within the predetermined range, a process is carried out to adjust the silicon concentration of the phosphoric acid aqueous solution flowing through the circulating line 3, or to change the phosphoric acid aqueous solution flowing through the circulating line 3.

Thus, according to the substrate treating apparatus 1 in Embodiment 1, the concentration measuring station 51 measures silicon concentration by potentiometry, which can measure silicon concentration in the phosphoric acid aqueous solution with high accuracy. The accuracy of measuring silicon concentration by potentiometry is hardly influenced by the temperature of the phosphoric acid aqueous solution. Therefore, even with the phosphoric acid aqueous solution drawn from the circulating line 3, silicon concentration can be measured appropriately.

The concentration measuring station 51, with the measuring vessel 53, measuring electrode 55, reference electrode 56 and potentiometric unit 57, can conveniently perform measurement by potentiometry.

The concentration measuring station 51, with the drain pipe 35, can conveniently dispose of the phosphoric acid aqueous solution used as object of measurement. This can reliably prevent the phosphoric acid aqueous solution and reagent used as object of measurement from returning to the circulating line 3.

The branch pipe 31 branching from the circulating line 3 can conveniently extract part of the phosphoric acid aqueous solution flowing through the circulating line 3. The concentration measuring station 51 carries out concentration measurement for the phosphoric acid aqueous solution extracted by the branch pipe 31. There is no possibility that the phosphoric acid aqueous solution and reagent used in the concentration measuring station 51 mix into the circulating line 3.

Particularly since the branch pipe 31 is joined to the pipeline 18 between the heater 15 for circulation and the filter 17, the phosphoric acid aqueous solution can be extracted immediately after passing through the heater 15 for circulation. That is, the phosphoric acid aqueous solution can be extracted at a relatively high temperature. This can conveniently inhibit silicon and other substances from depositing in the extracted phosphoric acid aqueous solution. As a result, lowering of the measurement accuracy in the concentration measuring station 51 can be inhibited conveniently. Further, the phosphoric acid aqueous solution can be extracted easily since the phosphoric acid aqueous solution can be extracted in a condition of relatively low viscosity (i.e. the phosphoric acid aqueous solution having a relatively high fluidity).

The switch valve 32 mounted on the branch pipe 31 can conveniently extract part of the phosphoric acid aqueous solution from the circulating line 3 while allowing the phosphoric acid aqueous solution to flow through the circulating line 3. The circulating line 3 includes no valve for extracting the phosphoric acid aqueous solution, thereby to inhibit an increase of pressure loss in the circulating line 3.

With the quantity measuring station 41 provided separately from the concentration measuring station 51, the measuring of the phosphoric acid aqueous solution and the measurement of silicon concentration can be carried out independently of each other. Therefore, for example, silicon concentration can be obtained efficiently by completing the measuring of the phosphoric acid aqueous solution before the measurement. Since the concentration measuring station 51 itself does not need to measure the phosphoric acid aqueous solution, the function and construction of the concentration measuring station 51 can be simplified.

The quantity measuring station 41 having the measuring tank 43 can measure the phosphoric acid aqueous solution conveniently.

Embodiment 2

Figure 2:
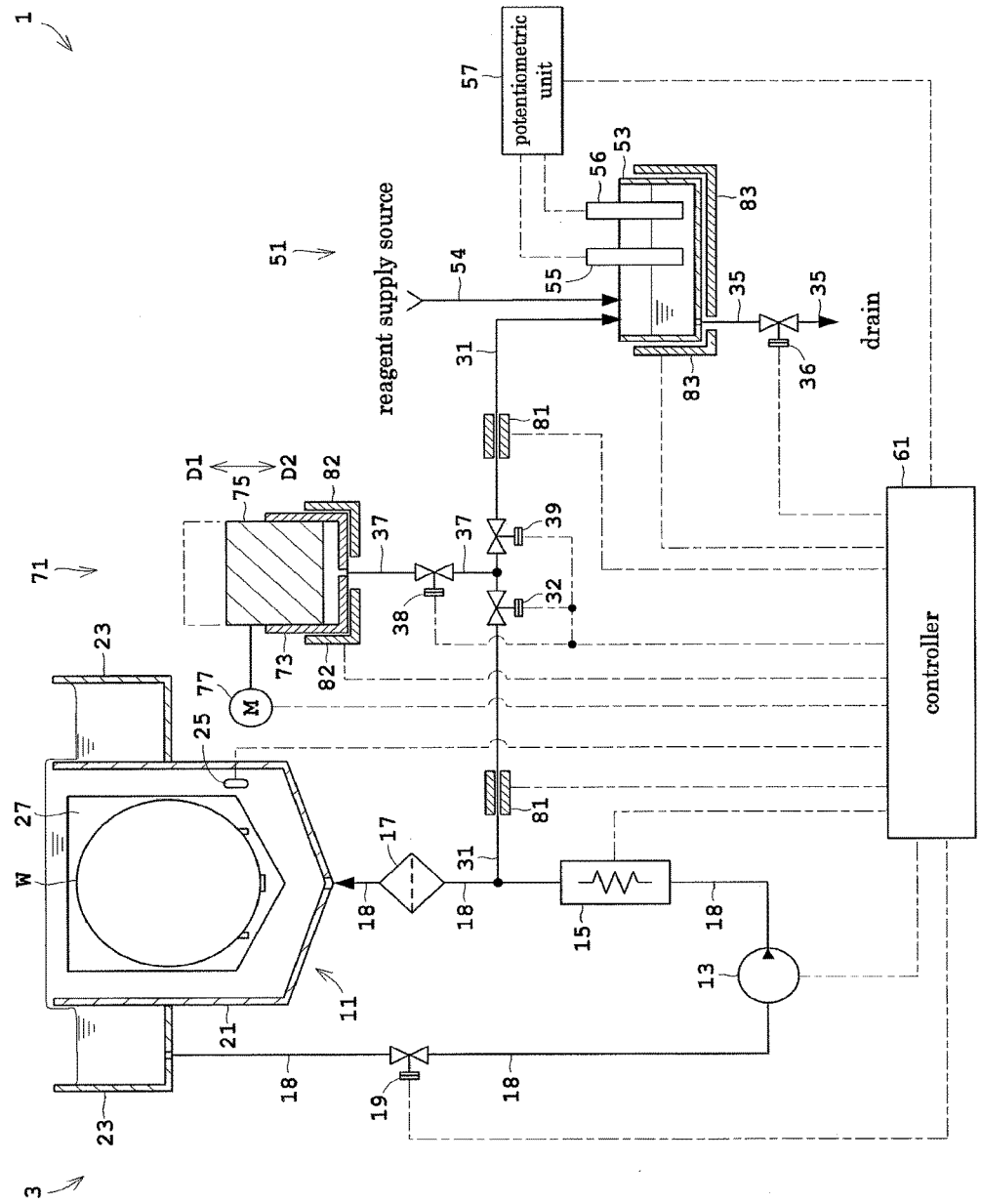
FIG. 2 is a view showing an outline construction of a substrate treating apparatus according to Embodiment 2.

Next, Embodiment 2 of this invention will be described. FIG. 2 is a view showing an outline construction of a substrate treating apparatus 1 according to Embodiment 2. Like reference signs are used to identify like parts which are the same as in Embodiment 1 and will not particularly be described.

The substrate treating apparatus 1 according to Embodiment 2 includes a quantity measuring station 71 in place of the quantity measuring station 41 in Embodiment 1. The quantity measuring station 71 is connected to piping 37 further branching from the branch pipe 31. The piping 37 branches from the branch pipe 31 in a position on the secondary side of the switch valve 32. The piping 37 has a switch valve 38 mounted in an intermediate position thereof. The branch pipe 31 further includes a switch valve 39 mounted in an intermediate position thereof. The switch valve 39 is disposed adjacent the secondary side of a junction of the branch pipe 31 and piping 37. The other end of the branch pipe 31 which is on the secondary side of the switch valve 39 is directly connected to the concentration measuring station 51.

The quantity measuring station 71 includes a syringe 73, a plunger 75 and a driver 77. The syringe 73 has a cylindrical shape. The plunger 75 is disposed in the syringe 73. The plunger 75 is slidable relative to the syringe 73 in an airtight state (FIG. 2 schematically shows moving directions D1 and D2 of the plunger 75). When the plunger 75 moves backward in the direction D1, the phosphoric acid aqueous solution is drawn into the syringe 73. When the plunger 75 moves forward in the direction D2, the phosphoric acid aqueous solution is discharged from the syringe 73. The driver 77 moves the plunger 75 backward and forward.

The substrate treating apparatus 1 includes heaters 81, 82 and 83 for sampling which heat the phosphoric acid aqueous solution extracted from the circulating line 3. The heaters 81 for sampling are mounted on the branch pipe 31 for heating the phosphoric acid aqueous solution in the branch pipe 31. The heater 82 for sampling is attached to the quantity measuring station 71 for heating the phosphoric acid aqueous solution in the quantity measuring station 71. Specifically, the heater 82 for sampling is attached to the syringe 73 for heating the phosphoric acid aqueous solution in the syringe 73. The heater 83 for sampling is attached to the concentration measuring station 51 for heating the phosphoric acid aqueous solution in the concentration measuring station 51. Specifically, the heater 83 for sampling is attached to the measuring vessel 53 for heating the solution in the measuring vessel 53.

The controller 61 further controls the above driver 77, switch valves 38 and 39 and heaters 81-83 for sampling. The controller 61 controls the heaters 81-83 for sampling, such that the temperature of the phosphoric acid aqueous solution extracted from the circulating line 3 substantially agrees with the temperature of the phosphoric acid aqueous solution flowing through the circulating line 3. A target value of each of the heaters 81, 82 and 83 for sampling (i.e. a target temperature of the phosphoric acid aqueous solution) is the same as the target value of the heater 15 for circulation.

Next, an example of operation of the substrate treating apparatus 1 according to Embodiment 2 will be described. Substrate treatment is the same as in Embodiment 1 and therefore its description is omitted, and only an example of operation relating to concentration measurement will be described.

The controller 61, in a state where the switch valves 32 and 38 are opened and the switch valves 36 and 39 are closed, controls the driver 77 to move the plunger 75 backward (to move it in the direction D1) to a predetermined position. Part of the phosphoric acid aqueous solution flowing through the circulating line 3 flows into the branch pipe 31. One of the heaters 81 for sampling heats the phosphoric acid aqueous solution flowing through the branch pipe 31. The phosphoric acid aqueous solution is drawn from the branch pipe 31 via the piping 37 into the syringe 73. In the syringe 73, the phosphoric acid aqueous solution is stored in a predetermined quantity corresponding to an amount of movement of the plunger 75. The phosphoric acid aqueous solution measured in the syringe 73 in this way is heated by the heater 82 for sampling.

Then, the controller 61, in a state where the switch valves 32 and 36 are closed and the switch valves 38 and 39 are opened, moves the plunger 75 forward (to move it in the direction D2) to a predetermined position. The phosphoric acid aqueous solution is discharged in a predetermined quantity from the syringe 73. The discharged phosphoric acid aqueous solution flows to the concentration measuring station 51 through the piping 37 and branch pipe 31. The other heater 81 for sampling heats the phosphoric acid aqueous solution flowing through the branch pipe 31.

The phosphoric acid aqueous solution supplied to the concentration measuring station 51 and the reagent supplied from the reagent feeder 54 are stored in the measuring vessel 53. The heater 83 for sampling heats the solution in the measuring vessel 53. The potentiometric unit 57 measures a potential difference between the measuring electrode 55 and reference electrode 56, and measures a silicon concentration based on this measurement result. The measurement result is outputted to the controller 61. Subsequently, the switch valve 36 is opened. The solution in the measuring vessel 53 is drained off through the drain pipe 35.

Thus, the substrate treating apparatus 1 in Embodiment 2 provides effects similar to those in Embodiment 1.

The substrate treating apparatus 1 in Embodiment 2, with the heaters 81-83 for sampling which heat the phosphoric acid aqueous solution extracted from the circulating line 3, can properly inhibit silicon and other substances from depositing in the phosphoric acid aqueous solution extracted from the circulating line 3. Therefore, lowering of the measurement accuracy in the concentration measuring station 51 can be inhibited conveniently.

Specifically, the heaters 81 for sampling mounted on the branch pipe 3 can conveniently heat the phosphoric acid aqueous solution flowing through the branch pipe 31. This can prevent lowering of the fluidity of the phosphoric acid aqueous solution, thereby conveniently allowing the phosphoric acid aqueous solution to flow through the branch pipe 31.

The heater 82 for sampling attached to the quantity measuring station 71 can heat the phosphoric acid aqueous solution measured in the quantity measuring station 71. This can inhibit silicon and other substances from depositing in the phosphoric acid aqueous solution, and the quantity measuring station 71 can measure the phosphoric acid aqueous solution with increased accuracy.

The heater 83 for sampling attached to the concentration measuring station 51 can heat the solution in the measuring vessel 53. Even if silicon and other substances deposited in the phosphoric acid aqueous solution, the silicon and other substances could be redissolved within the measuring vessel 53. This can properly prevent lowering of the measurement accuracy of the concentration measuring station 51.

Each of the heaters 81, 82 and 83 for sampling heats the extracted phosphoric acid aqueous solution to be the same temperature as the phosphoric acid aqueous solution flowing through the circulating line 3. Thus, the conditions of the phosphoric acid aqueous solution can be made substantially the same in the circulating line 3 and the concentration measuring station 51. Therefore, based on the measurement result of the concentration measuring station 51, the controller 61 can conveniently grasp the silicon concentration in the phosphoric acid aqueous solution flowing through the circulating line 3.

Embodiment 3

Figure 3:
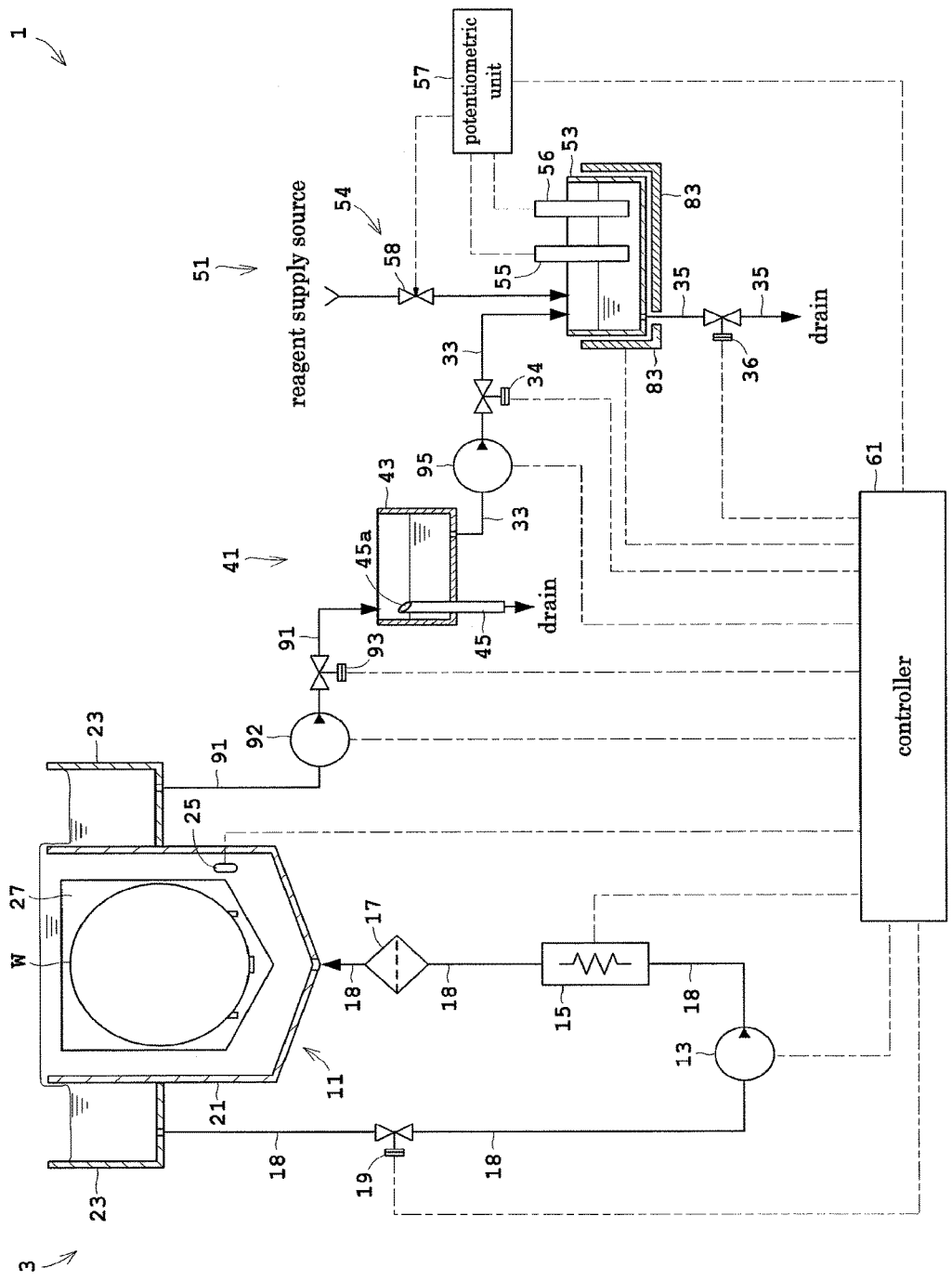
FIG. 3 is a view showing an outline construction of a substrate treating apparatus according to Embodiment 3.

Next, Embodiment 3 of this invention will be described. FIG. 3 is a view showing an outline construction of a substrate treating apparatus 1 according to Embodiment 3. Like reference signs are used to identify like parts which are the same as in Embodiments 1 and 2 and will not particularly be described.

The substrate treating apparatus 1 according to Embodiment 3 includes a branch pipe 91 in place of the branch pipe 31 in Embodiment 1. The branch pipe 91 branches from the circulating line 3, off from the outer tank 23. One end of the branch line 91 is connected to the bottom of the outer tank 23. The other end of the branch line 91 is connected to the quantity measuring station 41.

The branch pipe 91 has a first pump 92 mounted in an intermediate position thereof for feeding the phosphoric acid aqueous solution. A switch valve 93 is disposed on the secondary side of the first pump 92 and the primary side of the quantity measuring station 41.

The substrate treating apparatus 1 further includes a second pump 95 mounted in an intermediate position of the feed pipe 33. The second pump 95 feeds the phosphoric acid aqueous solution from the quantity measuring station 41 to the concentration measuring station 51.

The concentration measuring station 51 monitors a potential difference between the measuring electrode 55 and reference electrode 56 while titrating the phosphoric acid aqueous solution with the reagent, and terminates the titration when the potential difference becomes a predetermined value. Silicon concentration is measured based on the quantity of reagent used until termination of the titration. Thus, the concentration measuring station 51 in Embodiment 3 applies the reagent by what is called the electrometric titration method. In Embodiment 1, a fixed quantity of reagent is supplied in a different reagent supply method. However, the concentration measuring station 51 in Embodiment 3 also measures silicon concentration by potentiometry, and in this respect is the same as the concentration measuring station 51 in Embodiment 1.

In order to carry out such silicon concentration measurement, the reagent feeder 54 has a burette 58 for dripping the reagent, which is also capable of measuring the quantity (volume) of reagent dripped. The potentiometric unit 57 controls the burette 58 to supply (drip) the reagent to the measuring vessel 53, and measures a silicon concentration based on the quantity of reagent supplied from the burette 58.

The controller 61 further controls the first and second pumps 92 and 95 and the switch valve 93 noted above.

Next, an example of operation of the substrate treating apparatus 1 according to Embodiment 3 will be described. Substrate treatment is the same as in Embodiment 1 and therefore its description is omitted, and only an example of operation relating to concentration measurement will be described.

The controller 61 drives the first pump 92 in a state where the switch valve 93 is opened and the switch valves 34 and 36 are closed. Part of the phosphoric acid aqueous solution flowing through the circulating line 3 flows into the branch pipe 91. The phosphoric acid aqueous solution having flowed into the branch pipe 91 is supplied to the quantity measuring station 41. The quantity measuring station 41 measures a predetermined quantity of phosphoric acid aqueous solution. Subsequently, the first pump 92 is stopped and the switch valve 93 is closed.

Then, the controller 61 opens the switch valve 34, and drives the second pump 95. The predetermined quantity of phosphoric acid aqueous solution flows from the quantity measuring station 41 through the feed pipe 33 into the concentration measuring station 51 (measuring vessel 53). Subsequently, the controller 61 stops the second pump 95 and closes the switch valve 34.

The phosphoric acid aqueous solution supplied to the concentration measuring station 51 is stored in the measuring vessel 53. The solution in the measuring vessel 53 is heated by the heater 83 for sampling. The potentiometric unit 57, while monitoring a potential difference between the measuring electrode 55 and reference electrode 56, operates the burette 58 to drip the reagent to the phosphoric acid aqueous solution in the measuring vessel 53. When the potential difference becomes the predetermined value, the titration by the burette 58 is terminated. The potentiometric unit 57 measures a silicon concentration based on a titration quantity of reagent, and outputs the measurement result.

Thus, the substrate treating apparatus 1 in Embodiment 3 provides effects similar to those in Embodiments 1 and 2.

In the substrate treating apparatus 1 according to Embodiment 3, the branch pipe 91 branches from the circulating line 3, off from the outer tank 23. Therefore, even if part of the phosphoric acid aqueous solution flowing through the circulating line 3 is extracted, there is little influence on the flows of the phosphoric acid aqueous solution within the inner tank 6. Thus, silicon concentration can be measured while allowing the phosphoric acid aqueous solution to circulate appropriately.

With the first pump 92, the phosphoric acid aqueous solution can be extracted smoothly from the circulating line 3. This can increase the degree of freedom for arrangement of the branch pipe 91 and quantity measuring station 41.

With the second pump 95, the phosphoric acid aqueous solution can be fed smoothly from the quantity measuring station 41 to the concentration measuring station 51. This can increase the degree of freedom for arrangement of the quantity measuring station 41, feed pipe 33 and concentration measuring station 51.

Since the reagent feeder 54 includes the burette 58, the reagent can be used in titration by the electrometric titration method. This can hold down consumption of the reagent appropriately.

Embodiment 4

Figure 4:
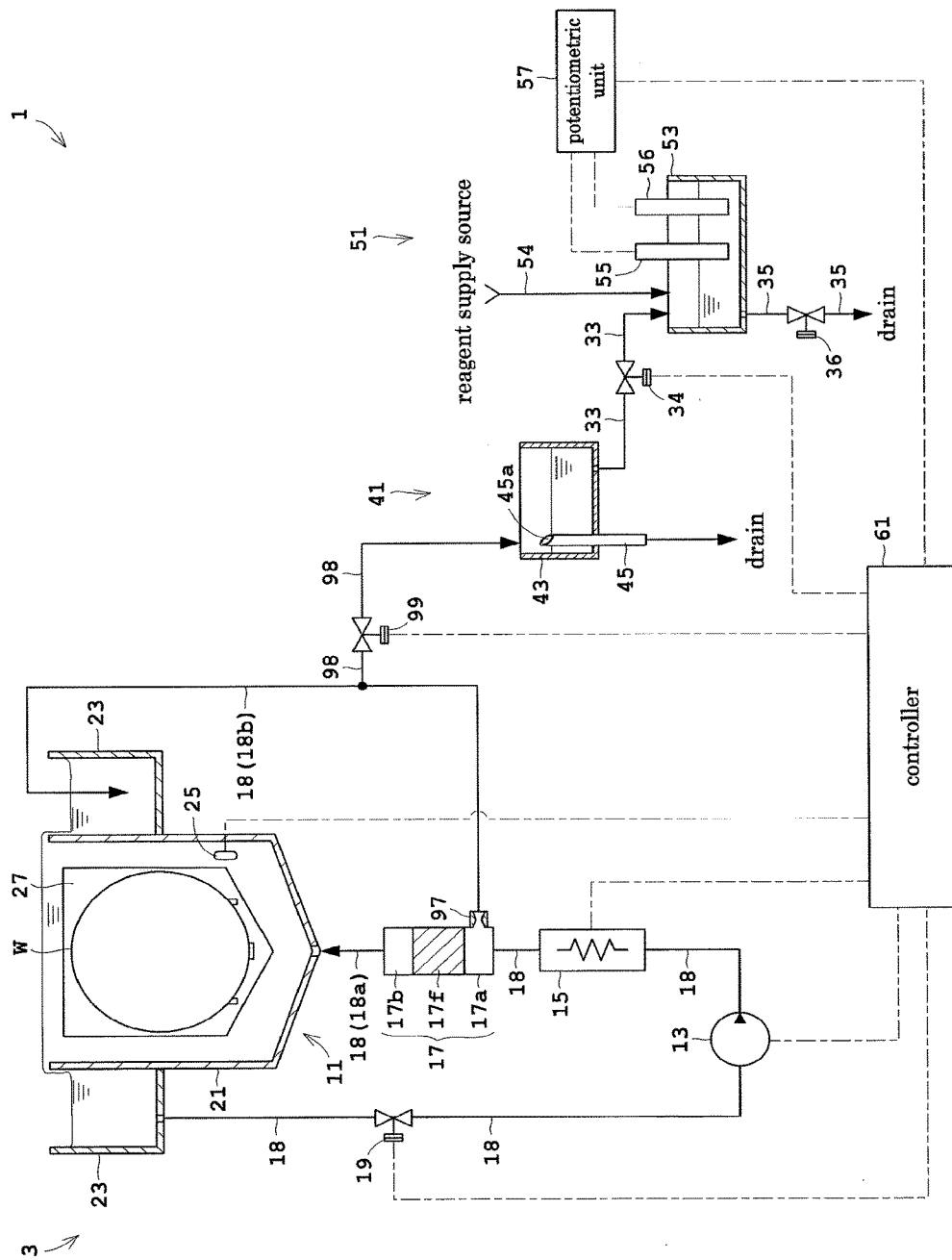
FIG. 4 is a view showing an outline construction of a substrate treating apparatus according to Embodiment 4.

Next, Embodiment 4 of this invention will be described. FIG. 4 is a view showing an outline construction of a substrate treating apparatus 1 according to Embodiment 4. Like reference signs are used to identify like parts which are the same as in Embodiments 1 through 3 and will not particularly be described.

Embodiment 4 provides two pipelines 18 (i.e. first piping 18a and second piping 18b) in parallel connection between the filter 17 and treating tank 11. The circulating line 3 has the two paths only through the section between the filter 17 and treating tank 11. This construction will particularly be described hereinafter.

The filter 17 includes an entrance portion 17a, an exit portion 17b, and a filter element 17f formed between these entrance portion 17a and exit portion 17b. The filter element 17f is a filtering medium for removing foreign substances. The entrance portion 17a stores the phosphoric acid aqueous solution before passing through the filter element 17*f*. The exit portion 17*b* stores the phosphoric acid aqueous solution after passing through the filter element 17*f*.

The exit portion 17*b* is connected to the inner tank 21 through the first piping 18*a*. The phosphoric acid aqueous solution flows from the exit portion 17*b* through the first piping 18*a* toward the inner tank 21

A discharge portion 97 is formed in the entrance portion 17*a*. The discharge portion 97 discharges gas generated within the entrance portion 17*a*. The discharge portion 97 has an orifice formed therein which constricts a flow path therethrough. The discharge portion 97 is connected to the outer tank 23 through the second piping 18*b*. The phosphoric acid aqueous solution flows from the entrance portion 17*a* through the second piping 18*b* toward the outer tank 23.

The substrate treating apparatus 1 in Embodiment 4 includes a branch pipe 98 in place of the branch pipe 31 in Embodiment 1. The branch pipe 98 branches from the second piping 18*b* forming the circulating line 3. One end of the branch pipe 98 is joined to the second piping 18*b*. The other end of the branch pipe 98 is connected to the quantity measuring station 41. The branch pipe 98 has a switch valve 99 mounted in an intermediate position thereof.

The controller 61 further controls the above switch valve 99.

Next, an example of operation of the substrate treating apparatus 1 according to Embodiment 4 will be described. Description will be made here centering on the flow of the phosphoric acid aqueous solution through the circulating line 3 or branch pipe 98.

The controller 61 drives the circulating pump 13 in a state where only the switch valve 19 is opened and the switch valves 34, 36 and 99 are closed. The phosphoric acid aqueous solution entering the filter 17 mainly flow through the filter 17 in the order of the entrance portion 17*a*, filter element 7*f* and exit portion 17*b*. The phosphoric acid aqueous solution having reached the exit portion 17*b* flows out of the filter 17 and into the inner tank 21 through the first piping 18*a*.

However, part of the phosphoric acid aqueous solution within the entrance portion 17*a* flows out into the second piping 18*b* through the discharge portion 97. When bubbles, foreign substances and so on (hereinafter called simply "bubbles and the like") which cannot easily enter the filter element 17*f* stagnate in the entrance portion 17*a*, these bubbles and the like are extruded along with the phosphoric acid aqueous solution into the second piping 18*b*.

The inside of the entrance portion 17*a* is maintained at a relatively high pressure by the filter element 17*f* and the orifice formed in the discharge portion 97. Therefore, the pressure of the phosphoric acid aqueous solution in the second piping 18*b* is higher than the pressure of the phosphoric acid aqueous solution in the first piping 18*a*. The flow rate of the phosphoric acid aqueous solution and other substances in the second piping 18*b* is held down by the orifice to be far lower than the flow rate of the phosphoric acid aqueous solution in the first piping 18*a*. That is, between the filter 17 and treating tank 11, the phosphoric acid aqueous solution flows mainly through the first piping 18*a*.

When the controller 61 opens the switch valve 99 while driving the circulating pump 13, the phosphoric acid aqueous solution flows from the second piping 18*b* (circulating line 3) into the branch pipe 98.

Thus, the substrate treating apparatus 1 in Embodiment 4 provides effects similar to those in Embodiment 1.

The substrate treating apparatus 1 according to Embodiment 4, with the branch pipe 98 branching from the second piping 18*b* at a higher pressure than the first piping 18*a*, can easily extract the phosphoric acid aqueous solution from the circulating line 3.

The phosphoric acid aqueous solution in the second piping 18*b* has a higher temperature than the phosphoric acid aqueous solution in the first piping 18*a* in that the former does not pass through the filter element 17*f*. Therefore, the phosphoric acid aqueous solution can be extracted from the circulating line 3 in the condition of having the higher temperature.

This invention is not limited to the foregoing embodiments, but may be modified as follows:

(1) Each of Embodiments 1 through 4 described above has shown the construction of the quantity measuring station 41 or 71 by way of example, but the invention is not limited thereto. For example, a change may be made to a quantity measuring station having a measuring tank for storing the phosphoric acid aqueous solution, and a level sensor for detecting a liquid level of the phosphoric acid aqueous solution in the measuring tank. Such modified embodiment can also measure the phosphoric acid aqueous solution with high accuracy.

(2) Each of Embodiments 1 through 4 described above provides the quantity measuring station 41 or 71 separately from the concentration measuring station 51, but the invention is not limited thereto. That is, a change may be made to a concentration measuring station having the function for measuring the phosphoric acid aqueous solution, with the quantity measuring station 41 and associated components omitted. For example, the concentration measuring station may be modified to further include an overflow pipe for adjusting the phosphoric acid aqueous solution in the measuring vessel 53 to a predetermined quantity. Or the concentration measuring station may be modified to further include a level sensor for detecting a liquid level of the phosphoric acid aqueous solution in the measuring vessel 53.

(3) Embodiment 2 has not described a specific construction of the heaters 81 for sampling. Heaters of any arbitrary construction can be employed as long as they heat the phosphoric acid aqueous solution in the branch pipe 31. For example, heaters arranged on outer surfaces of the branch pipe 31 may be used. Or the heaters may be arranged in the branch pipe 31 (that is, in the flow path of the phosphoric acid aqueous solution). Or the branch pipe 31 employed may have a double pipe structure, with an outer pipe providing an annular flow path of the phosphoric acid aqueous solution, and with heaters arranged in a circular inner pipe.

(4) Embodiment 2 described above provides the heaters 81-83 for sampling, but the invention is not limited thereto. As long as the phosphoric acid aqueous solution extracted from the circulating line 3 can be heated, the installation sites of the heaters can be selected or changed as appropriate. For example, heaters may be arranged along all of the flow paths of the phosphoric acid aqueous solution extracted from the circulating line 3, or along only part of the flow paths of the phosphoric acid aqueous solution. One or two of the heaters 81-83 for sampling may be omitted. Specifically, Embodiment 1, for example, may be modified to include a heater for sampling which heats the quantity measuring station 41 (e.g. measuring tank 43).

(5) In Embodiment 3 described above, one end of the branch pipe 91 is connected to the bottom of the outer tank 23. This is not limitative. The position of one end of the branch pipe 91 may be changed to any arbitrary position in the outer tank 23. For example, one end of the branch pipe 91 may be positioned in an upper part of the outer tank 23 or a relatively high position in the outer tank 23. With such arrangement, an upper part (or a part adjacent the surface) of the upper phosphoric acid aqueous solution may be drawn from the outer tank 23. With such arrangement, the phosphoric acid aqueous solution can be extracted in a condition of higher temperature. Further, one end of the branch pipe 91 may be located in a position in the outer tank 23 relatively close to the outer wall of the inner tank 21. This allows the phosphoric acid aqueous solution to be drawn from a position of relatively little influence of heat radiation, and thus the phosphoric acid aqueous solution at high temperature can be extracted stably.

(6) In Embodiment 3 described above, the branch pipe 91 branches from the circulating line 3, off from the outer tank 23, but the invention is not limited thereto. That is, a change may be made to a branch pipe branching from any arbitrary component (11, 13, 15, 17, 18) included in the circulating line 3.

(7) In Embodiment 1 described above, the switch valve 32 is mounted on the branch pipe 31, but the invention is not limited thereto. A modification may be made to include a selector valve at the joint of the branch pipe 31 and circulating line 3 (pipeline 18) for switching the flow path of the phosphoric acid aqueous solution. With this modification, the flow path of the phosphoric acid aqueous solution can be switched conveniently between the circulating line 3 and branch pipe 31.

(8) In each of Embodiments 1 through 4 described above, the treating tank 11 has the inner tank 21 and outer tank 23, but the invention is not limited thereto. For example, the outer tank 23 may be omitted.

(9) The embodiments and their modifications described above may be combined in various ways as appropriate.

This invention may be embodied in other specific forms without departing from the spirit or essential attributes thereof and, accordingly, reference should be made to the appended claims, rather than to the foregoing specification, as indicating the scope of the invention.

What is claimed is:

1. A substrate treating method for carrying out etching treatment of substrates, comprising:
    a treating step including causing a phosphoric acid aqueous solution to flow through a circulating line of a substrate treating apparatus to carry out the etching treatment of the substrates in a treating tank on the circulating line;
    the treating step including a circulating step of circulating the phosphoric acid aqueous solution through the circulating line from the treating tank, then through a heater for circulation, then through a filter, and then back to the treating tank;
    an extracting step including extracting the phosphoric acid aqueous solution flowing through the circulating line from a position after the heater for circulation and before the filter on the circulating line, and feeding the phosphoric acid aqueous solution into a measuring tank;
    a quantity measuring step including adjusting the phosphoric acid aqueous solution in the measuring tank to a predetermined quantity;
    a concentration measuring step including feeding all the phosphoric acid aqueous solution adjusted in the quantity measuring step from the measuring tank into a measuring vessel, and measuring silicon concentration in the phosphoric acid aqueous solution in the measuring vessel by potentiometry; and
    a determining step executed by a controller of the substrate treating apparatus and including determining subsequent treatment based on the silicon concentration measured;
    wherein the concentration measuring step measures a potential difference between a measuring electrode contacting the solution in the measuring vessel, and a reference electrode contacting the solution in the measuring vessel; and
    the concentration measuring step monitors the potential difference between the measuring electrode and the reference electrode while titrating the phosphoric acid aqueous solution in the measuring vessel with the reagent, terminates titration when the potential difference becomes a predetermined value, and measures the silicon concentration based on a quantity of the reagent used until termination of the titration.

2. The substrate treating method according to claim 1, wherein the quantity measuring step discharges a part exceeding the predetermined quantity of the phosphoric acid aqueous solution through an overflow pipe inserted into the measuring tank.

3. The substrate treating method according to claim 2, wherein the overflow pipe is inserted through a bottom of the measuring tank, upward into the interior of the measuring tank, and the quantity measuring step discharges the part exceeding the predetermined quantity of the phosphoric acid aqueous solution from the measuring tank through an opening formed in the overflow pipe at a predetermined height position above said bottom of the measuring tank.

4. The substrate treating method according to claim 3, wherein the opening is constantly open.

5. The substrate treating method according to claim 3, wherein the height position of the opening corresponds to a liquid level of the predetermined quantity of the phosphoric acid aqueous solution in the measuring tank.

6. The substrate treating method according to claim 1, wherein:
    the quantity measuring step adjusts the phosphoric acid aqueous solution in the measuring tank to the predetermined quantity in a state where a switch valve mounted on a feed pipe interconnecting the measuring tank and the measuring vessel is closed; and
    the concentration measuring step transfers all the phosphoric acid aqueous solution from the measuring tank to the measuring vessel by opening the switch valve.

7. The substrate treating method according to claim 1, wherein the concentration measuring step adds a reagent to the phosphoric acid aqueous solution in the measuring vessel.

8. The substrate treating method according to claim 1, wherein the quantity measuring step and the concentration measuring step are carried out independently of each other.

9. The substrate treating method according to claim 1, wherein the concentration measuring step heats the phosphoric acid aqueous solution in the measuring vessel by a heater attached to the measuring vessel.

10. The substrate treating method according to claim 1, wherein the concentration measuring step heats the phosphoric acid aqueous solution in the measuring vessel to a temperature substantially in agreement with a temperature of the phosphoric acid aqueous solution in the treating tank.

11. The substrate treating method according to claim 1, wherein the determining step, when the silicon concentration measured is within a predetermined range, determines to continue etching treatment using the phosphoric acid aqueous solution; and when the silicon concentration measured is outside the predetermined range, determines to carry out at least one of a process for adjusting the silicon concentration of the phosphoric acid aqueous solution and a process for changing the phosphoric acid aqueous solution.

12. The substrate treating method according to claim 1, wherein the concentration measuring step, while dripping the reagent from a burette to the phosphoric acid aqueous solution in the measuring vessel, measures a quantity of the reagent dripped.

* * * * *

UNITED STATES PATENT AND TRADEMARK OFFICE
CERTIFICATE OF CORRECTION

| | | |
|---|---|---|
| PATENT NO. | : 10,520,416 B2 | Page 1 of 1 |
| APPLICATION NO. | : 15/438341 | |
| DATED | : December 31, 2019 | |
| INVENTOR(S) | : Takahashi et al. | |

It is certified that error appears in the above-identified patent and that said Letters Patent is hereby corrected as shown below:

On the Title Page

Item (72) should read:
Tomohiro Takahashi, Kyoto (JP);
Hiroyuki Araki, Kyoto (JP);
Eugene Shalyt, Washington Township, NJ (US)

Signed and Sealed this
Eleventh Day of January, 2022

Drew Hirshfeld
*Performing the Functions and Duties of the*
*Under Secretary of Commerce for Intellectual Property and*
*Director of the United States Patent and Trademark Office*